(12) United States Patent
Kolb et al.

(10) Patent No.: US 9,623,231 B2
(45) Date of Patent: Apr. 18, 2017

(54) DEVICE TO TREAT INCONTINENCE

(71) Applicant: Elidah, Inc., Monroe, CT (US)

(72) Inventors: Eric Kolb, Sandy Hook, CT (US); Gloria Kolb, Sandy Hook, CT (US)

(73) Assignee: Elidah, LLC, Sandy Hook, CT (US)

( * ) Notice: Subject to any disclaimer, the term of this patent is extended or adjusted under 35 U.S.C. 154(b) by 0 days.

(21) Appl. No.: 14/678,058

(22) Filed: Apr. 3, 2015

(65) Prior Publication Data

US 2015/0290450 A1  Oct. 15, 2015

Related U.S. Application Data

(60) Provisional application No. 61/979,065, filed on Apr. 14, 2014.

(51) Int. Cl.
*A61N 1/04* (2006.01)
*A61N 1/36* (2006.01)

(52) U.S. Cl.
CPC ......... *A61N 1/0452* (2013.01); *A61N 1/0476* (2013.01); *A61N 1/36007* (2013.01); *A61N 1/36014* (2013.01); *A61N 1/0484* (2013.01)

(58) Field of Classification Search
CPC ............... A61N 1/0452; A61N 1/0476; A61N 1/36007; A61N 1/36014; A61N 1/0484
USPC .............................................. 607/40–41, 138
See application file for complete search history.

(56) References Cited

U.S. PATENT DOCUMENTS

| | | | |
|---|---|---|---|
| 4,742,833 A | 5/1988 | Barsom | |
| 5,562,717 A | 10/1996 | Tippey et al. | |
| 5,871,534 A | 2/1999 | Messick et al. | |
| 6,553,266 B1 * | 4/2003 | Yuang | A61N 1/0452 607/138 |
| 6,756,521 B1 | 6/2004 | Breitkopf | |
| 7,280,873 B2 | 10/2007 | Freed et al. | |
| 7,855,653 B2 * | 12/2010 | Rondoni | A61F 13/42 340/539.12 |
| 7,925,323 B2 | 4/2011 | Meyer | |
| 8,634,920 B2 | 1/2014 | Hagege | |
| 8,738,112 B2 | 5/2014 | Choe et al. | |
| 2005/0154438 A1 | 7/2005 | Fuller et al. | |
| 2013/0327342 A1 | 12/2013 | Watschke et al. | |
| 2014/0005752 A1 | 1/2014 | Hershey | |

OTHER PUBLICATIONS

International Search Report and Written Opinion dated Jun. 22, 2015 (PCT/US2015/025500).

* cited by examiner

*Primary Examiner* — Paula J Stice
(74) *Attorney, Agent, or Firm* — Alix, Yale & Ristas, LLP

(57) ABSTRACT

A skin surface electrode used in the treatment of incontinence. The electrode has one or more conductive regions and an egress through which bodily fluid may pass without substantially adversely affecting tissue contact in the conductive regions of the electrode. The electrode is configured for placement proximate a patient's perineal tissues. An incontinence treatment system includes an electrode, wearable signal generator and interface module.

19 Claims, 18 Drawing Sheets

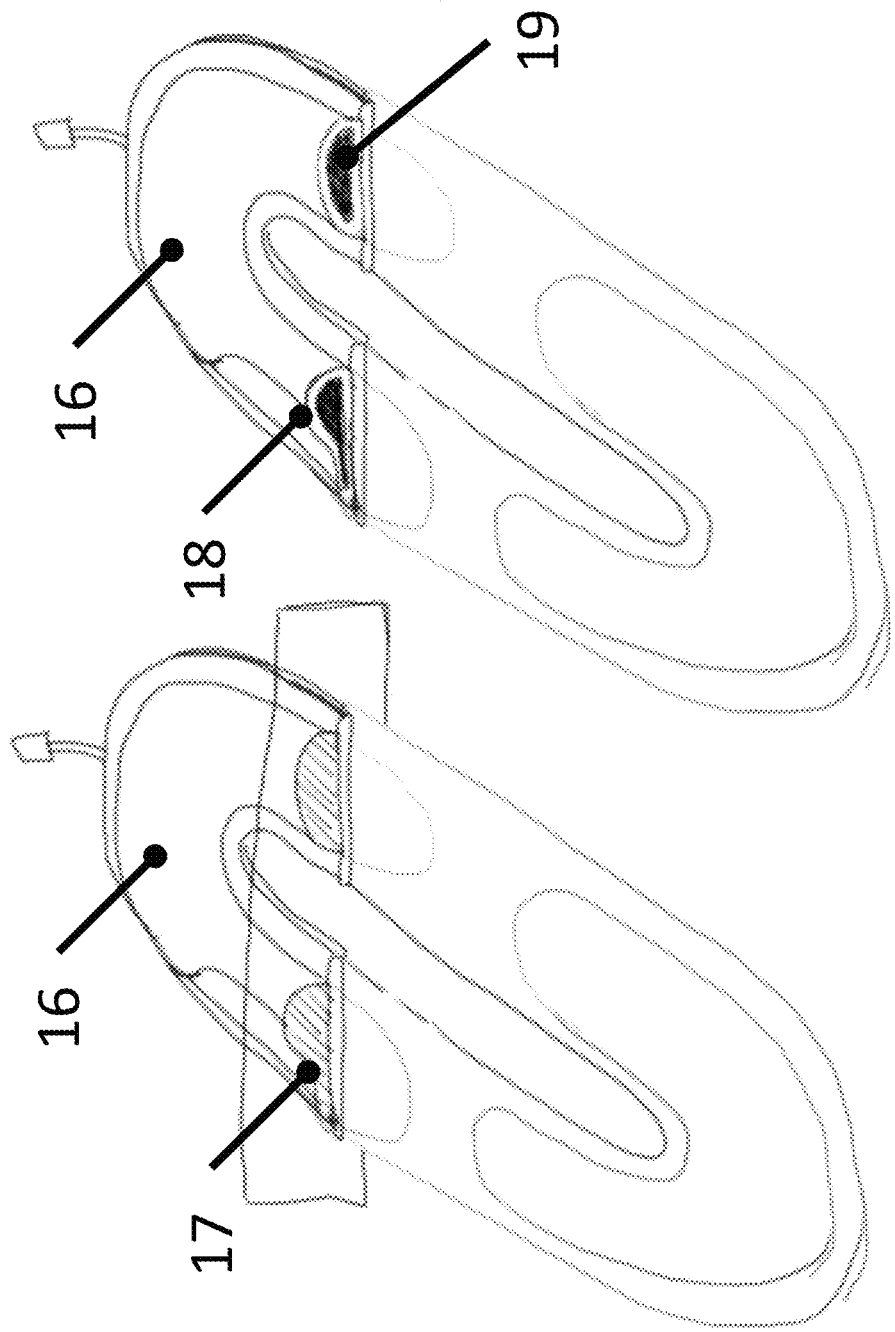

DEVICE TO TREAT INCONTINENCE

CROSS-REFERENCE TO RELATED APPLICATION

This application claims priority to U.S. Provisional Patent Application No. 61/979,065, for Device to Treat Incontinence, filed Apr. 14, 2014, the entire disclosure of which is hereby incorporated by reference.

FIELD OF INVENTION

The disclosure relates to an incontinence treatment device that utilizes transcutaneous electrical muscle stimulation to train and tone the muscle groups that control continence. Aspects described therein serve to drive improved patient compliance relative to known treatments.

BACKGROUND OF INVENTION

Electric muscle stimulation (EMS) has proven an effective tool for toning and retraining muscles. Important to its efficacy is the ability to stimulate the specific muscles, and this is complicated when the targeted muscles are deep within the patient's tissue. Several factors impact the ability of the delivered electric current to stimulate deep tissue muscles including the shape and frequency of the pulse waveform, the electrode size and configuration, positioning of the electrodes, and the continuity of the electrode-skin interface.

Urinary incontinence affects as many as one third of woman over the age of 30. One cause is a weakening of pelvic floor muscles. Clinical studies have shown EMS to be effective at resolving the symptoms of incontinence; however, two thirds of women who suffer from incontinence forgo medical treatment. Their failure to adopt or comply with EMS treatment regimens is at least partly due to the manner in which the stimulation is provided. One known method is through surgical implantation of a sacral nerve stimulator. Such implantable devices are relatively permanent and pose inherent risks including infection. EMS is also commonly provided via an intravaginal probe. Many women have psychological and physiological challenges accepting this form of treatment. Further, its configuration necessitates usage in a private location, limiting many patients' ability to obtain treatment multiple times per day. Thirdly, conventional EMS electrode pads can be applied to the perineal tissues of the patient in patterns aimed at stimulating the pelvic floor muscles. This commonly requires four electrode pads and placement by a trained clinician. As with the other stimulation devices, these surface electrodes have proven effective, but they are difficult for an individual to apply to herself, are difficult to maintain in contact for an extended period of time, are difficult to administer multiple times per day, fail to accommodate leakage, and do not allow discreet use.

Thus a need exists for a device to deliver EMS treatment to the pelvic floor that is easy to apply, can be worn for an extended period of time, allows multiple convenient treatments per day, can accommodate leakage and be worn discreetly by the user.

SUMMARY OF INVENTION

The device is used to treat incontinence by application of electronic muscle stimulation (EMS) to the muscle groups that control continence, including the pelvic floor muscles. Different from other incontinence devices which apply an electric pulse through a vaginal or anal probe, this device applies the electric pulse through a transcutaneous electrode applied to the perineal tissues, eliminating the need for intravaginal or intra-anal probes.

One embodiment of the device is an electrode that incorporates an egress through which bodily fluid may pass without substantially adversely affecting tissue contact in the conductive regions of the electrode. In certain embodiments this egress may be positioned to allow bodily fluid to pass freely from the external urethral opening or vagina to an absorbent pad underlying the electrode component.

Another embodiment of the device is an EMS system that includes an electrode with egress for bodily fluids, a wearable control unit or pulse generator, and interface module. In this embodiment the wearable pulse generator is configured to be worn and concealed against or under the user's clothing. During and/or between uses the wearable pulse generator interfaces with the interface module, permitting inter alia user manipulation of treatment settings.

BRIEF DESCRIPTION OF DRAWINGS

Aspects of the preferred embodiments will be described in reference to the drawings, wherein like reference numerals reflect like elements throughout:

FIG. 5a is a section view of an electrode embodiment.

FIG. 5b is a section view of an electrode embodiment.

DETAILED DESCRIPTION OF A PREFERRED EMBODIMENTS

The disclosed embodiments facilitate pelvic floor muscle contraction through electrical muscle stimulation delivered through the perineal tissues. For the purpose of this disclosure the term pelvic floor muscles refers to all musculature and associated nerves that act in maintaining continence. Further, for purpose of this disclosure the term perineal tissue(s) is intended to include the broad area of superficial tissue in the region of the perineum.

The particularly preferred embodiments are configured primarily to treat female stress or mixed urinary incontinence. However, certain embodiments of the electrode and system may effectively treat urge incontinence, male urinary incontinence, pelvic prolapse, vulvodynia, complications following prostate removal and fecal incontinence.

Figure 1:
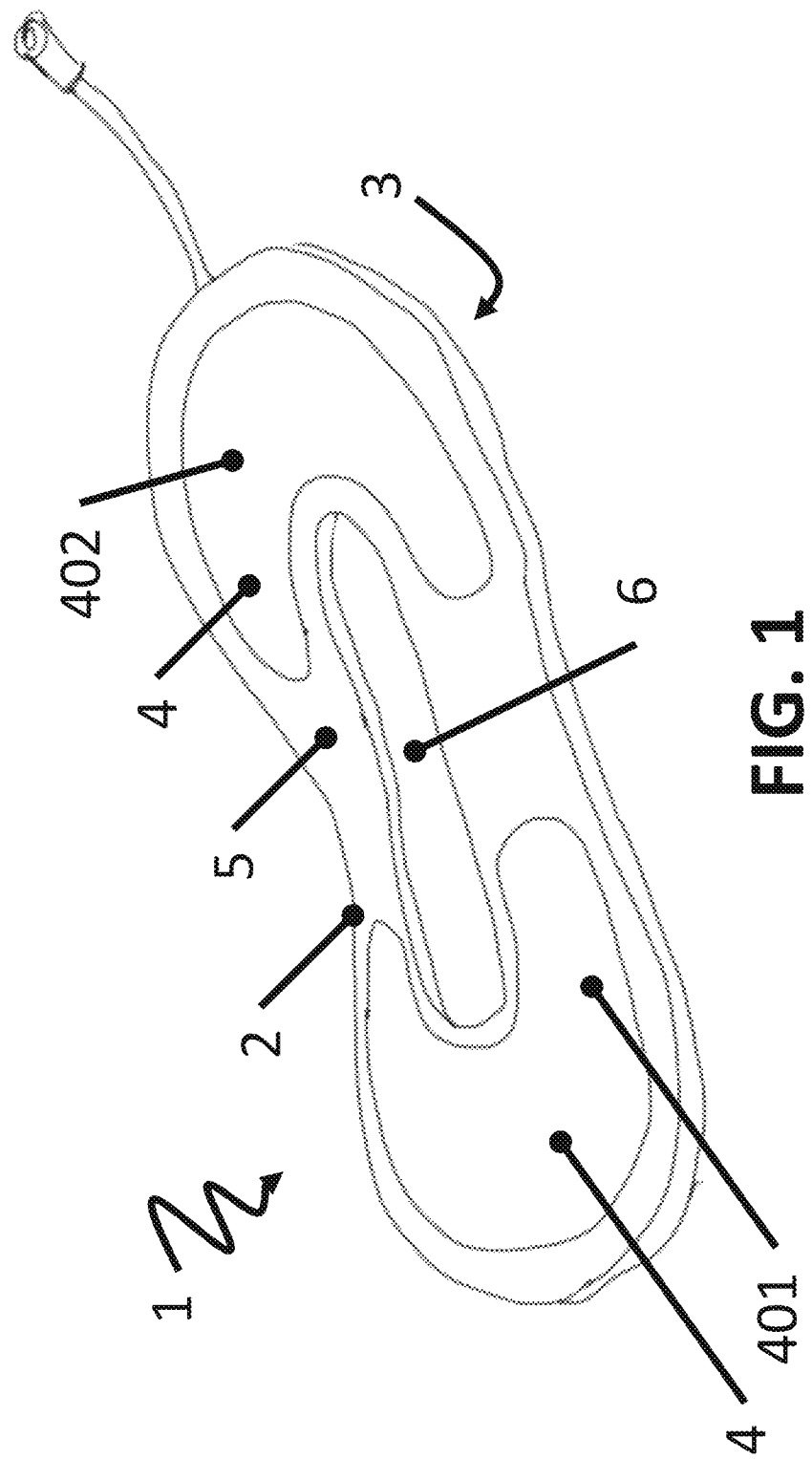
FIG. 1 is a perspective view of an electrode embodiment according to the disclosure.
Figure 2:
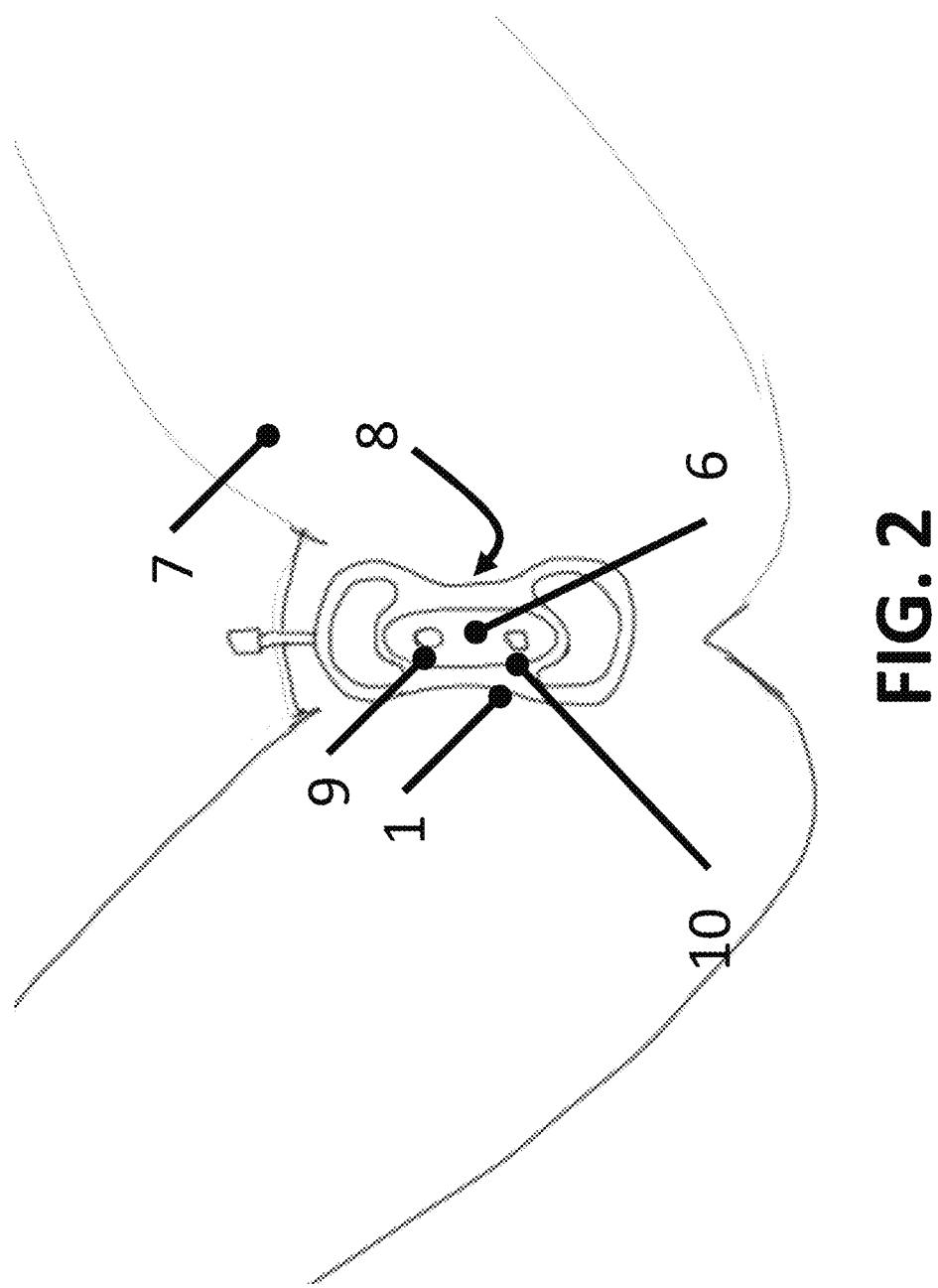
FIG. 2 is a view depicting an electrode embodiment positioned over the perineal tissue.

Referring to FIG. 1, the subject electrode 1 is depicted with a body comprising a skin contacting side or surface 2 and an outward facing non-contact side or surface 3. The skin contacting surface 2 includes one or more conductive regions 4 and one or more non-conductive (i.e. insulated) regions 5. The outward facing surface 3 is substantially electrically insulated from the conductive regions 4. Further, the electrode 1 includes an egress 6 at an intermediate position, and preferentially along its midline. Referring to FIG. 2, when the electrode 1 is positioned against the skin 7 and over the perineal tissue 8 such that the egress 6 is centered over the external urethral opening 9, vagina 10 and/or anus, the egress 6 allows bodily fluid to flow past the electrode 1 without substantially interrupting contact between the skin contacting surface 2 and the skin 7.

In one embodiment a first conductive region 401 serves as an anode and a second conductive region 402 serves as a cathode. When connected to an EMS device current flows from the anode, through the user's tissue and into the cathode. In this embodiment the conductive regions of the electrode are electrically isolated from one another and spaced sufficiently to allow the electrical current to penetrate to the depth of the pelvic floor muscles.

Figure 3:
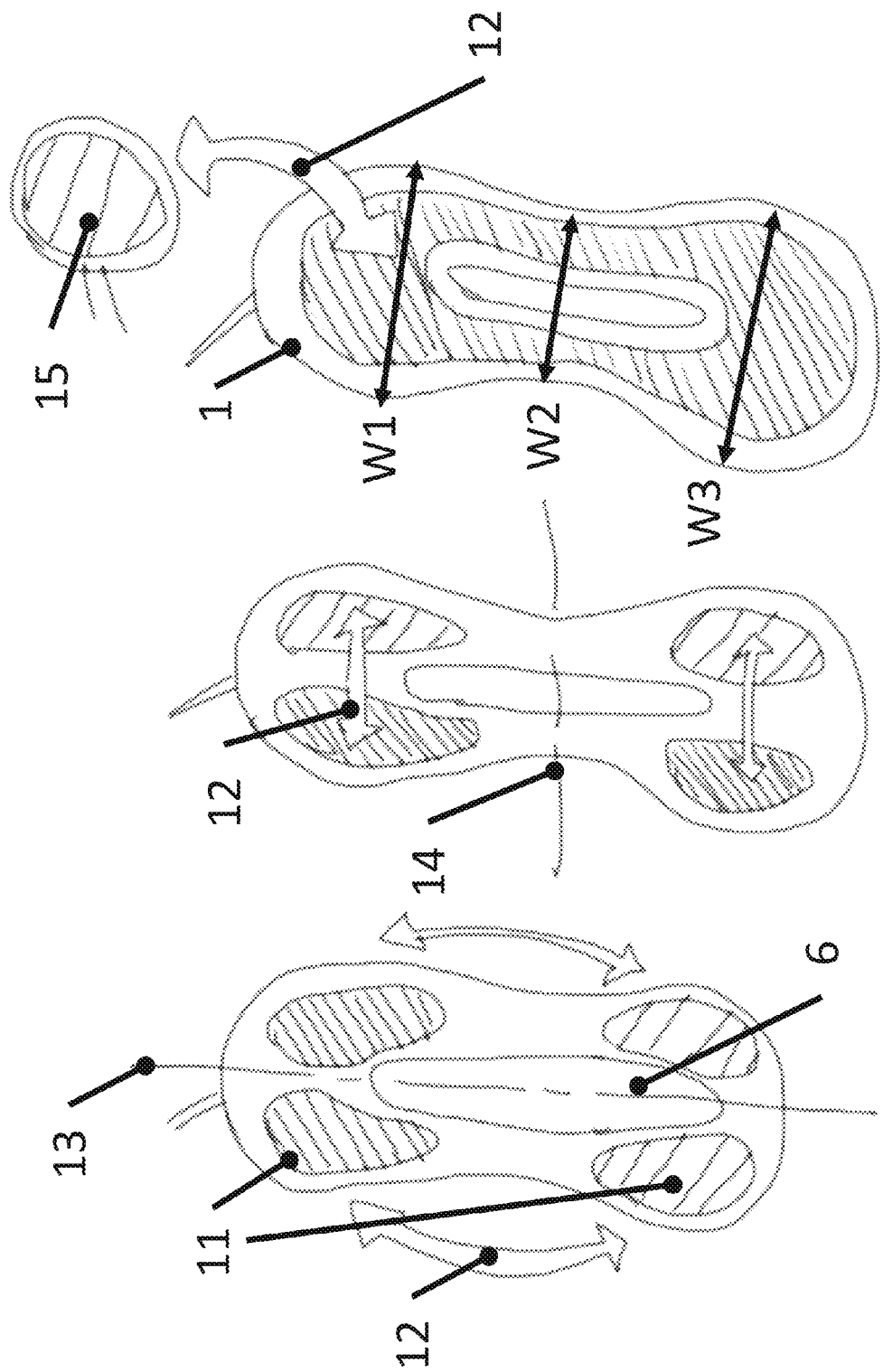
FIG. 3 is a view depicting several alternate embodiments of the disclosed electrode.

Referring to FIG. 3, in one embodiment an anode-cathode pair 11 is located laterally on each side of the egress 6 such that current 12 flows along a sagittal plane 13. In another embodiment an anode is located on one lateral side of the electrode and the corresponding cathode is located on the opposing lateral side such that current 12 flows along a coronal plane 14. In yet another embodiment the subject perineal tissue contacting electrode 1 includes an anode but no corresponding cathode. For this embodiment a separate conventional electrode 15 placed elsewhere on the patient serves as the cathode.

Figure 4:
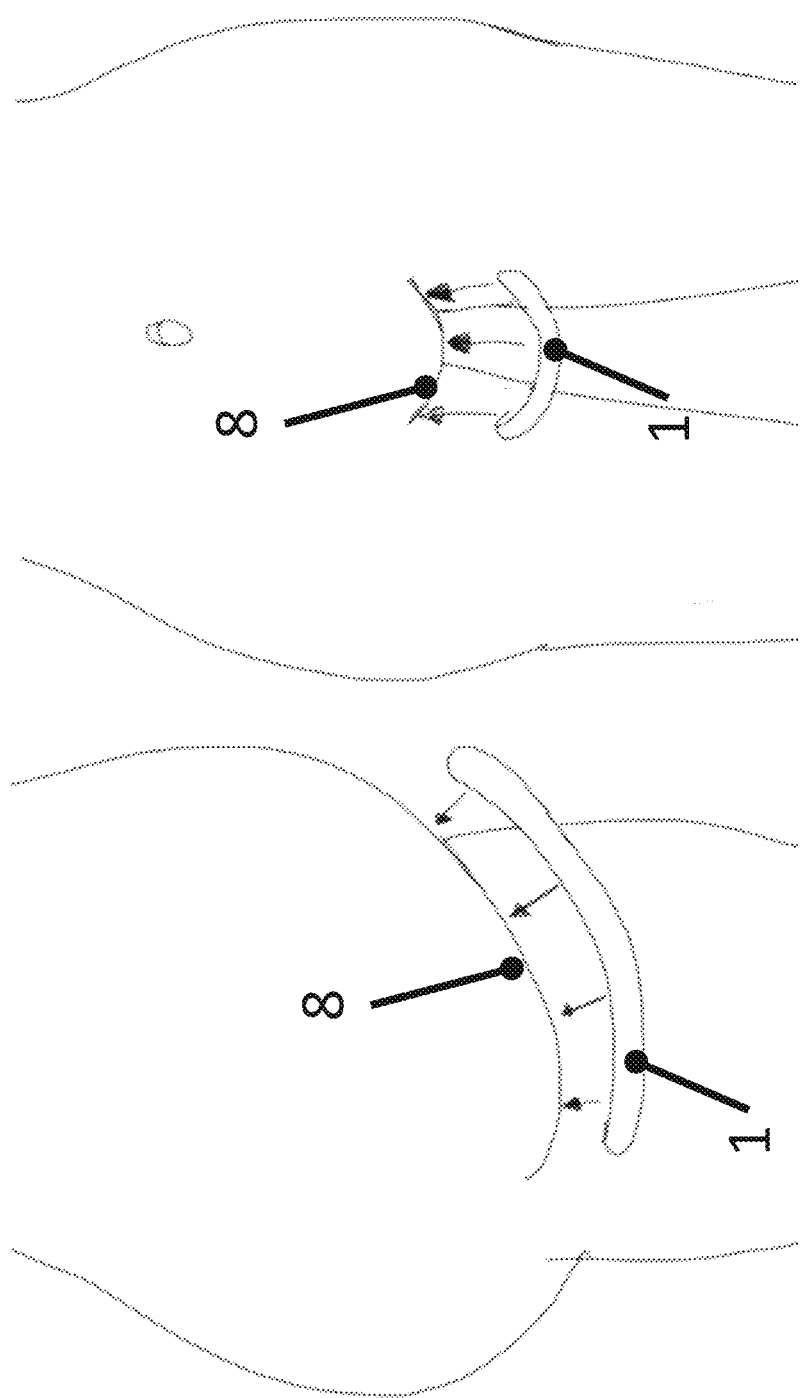
FIG. 4 is a lateral and anterior view depicting placement of an electrode embodiment.

The shape of the perineal tissue varies from patient to patient and also changes with changing body position, for example moving from a seated to standing position. However, conventional electrodes are substantially flat and circular or rectangular in shape. Given the contoured shape of the perineal tissue such conventional electrodes are not well suited for maintaining electrode-skin contact. Still referring to FIG. 3, the embodiment of the electrode 1 has a generally hourglass shape (i.e. profile) with an outer edge periphery that tapers inward toward a longitudinal intermediate portion, generally defining three lateral widths (W1, W2, W3), wherein W2 is located between and is less than W1 and W3. Referring to FIG. 4, in one embodiment the subject electrode 1 is contoured to fit the perineal tissue 8. For example, the skin contacting surface of the electrode may have a predefined curvature to accommodate anatomic curvature in the sagittal plane. Similarly, the skin contacting surface may be concave in the coronal plane to accommodate labial tissue.

Referring to FIG. 5a, in one embodiment the conductive region 16 is composed of a compliant conductive polymer 17 that is locally compressible to accommodate the user's anatomy. In one embodiment this conductive polymer has a local thickness of greater than 2 mm. In another embodiment (FIG. 5b) the conductive region comprises a conductive pouch 18 filled with a conductive liquid, gel or foam 19. The filled pouch construct permits local deformation of the conductive region to accommodate varied user anatomy. Similarly, non-conductive regions of the electrode may also comprise a filled pouch construct to permit local deformation and conformity with user anatomy. Maintaining the electrode-tissue contact in the non-conductive region is beneficial in that it typically inhibits fluid from accumulating along the skin. An additional advantage of the conductive fluid, gel or foam 19 filled pouch configuration is that the user can place the electrode in a refrigerator freezer prior to use. The cooled electrode may then act as a cold compress for local treatment of pain in nerves during treatment.

Figure 7:
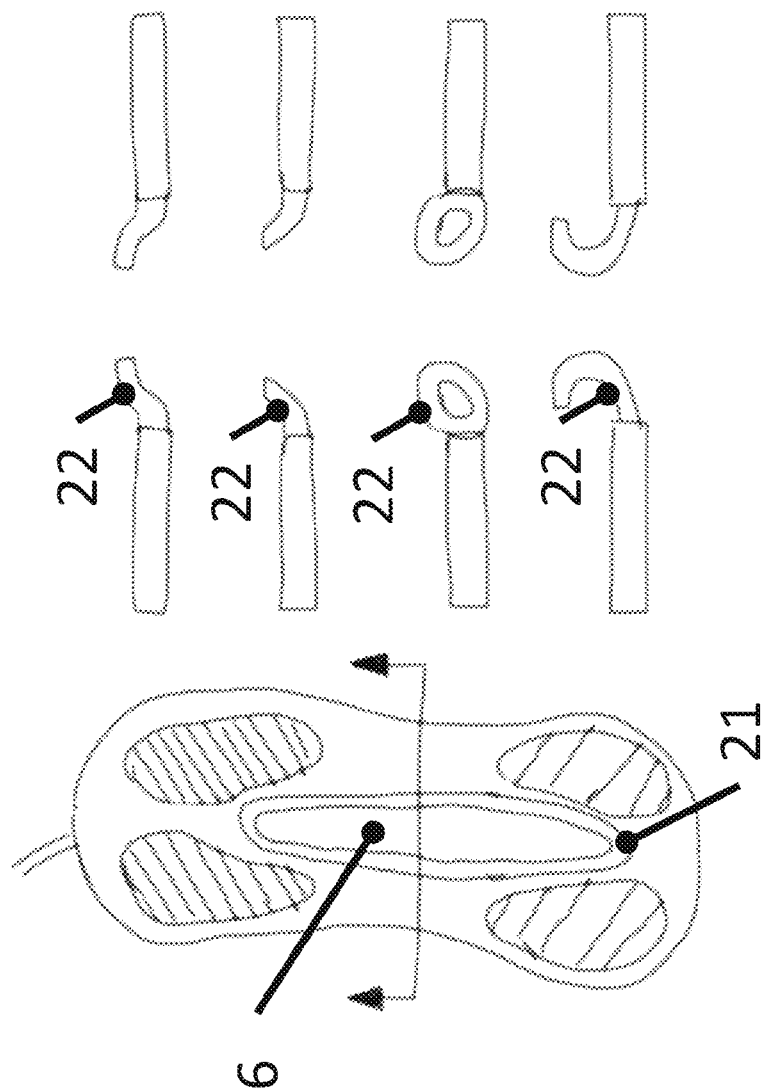
FIG. 7 is a section view of several alternate electrode embodiments, showing different geometries of the egress.
Figure 6:
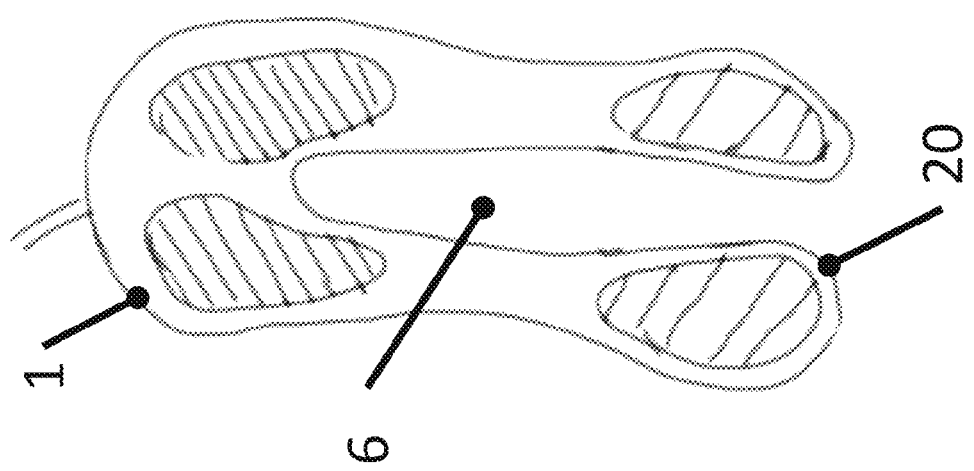
FIG. 6 shows another embodiment of the disclosed electrode.

The egress can have various peripheral shapes, including circular, ovular, triangular, rectangular, or combinations thereof. Referring to FIG. 6, in one embodiment the egress 6 extends through the posterior edge 20 of the electrode 1. Referring to FIG. 7, in another embodiment the periphery 21 of the egress 6 has geometry and material compliance sufficient to act as a gasket 22 and resist flow of bodily fluid along the electrode-skin interface. Various gasket geometries are depicted in the cross-sectional views in FIG. 7.

In another embodiment the non-conductive region is comprised of a material and structure that wicks moisture away from the skin-electrode interface. For example, the non-conductive region could be constructed of a wicking fabric or an absorbent hydrogel.

Figure 8:
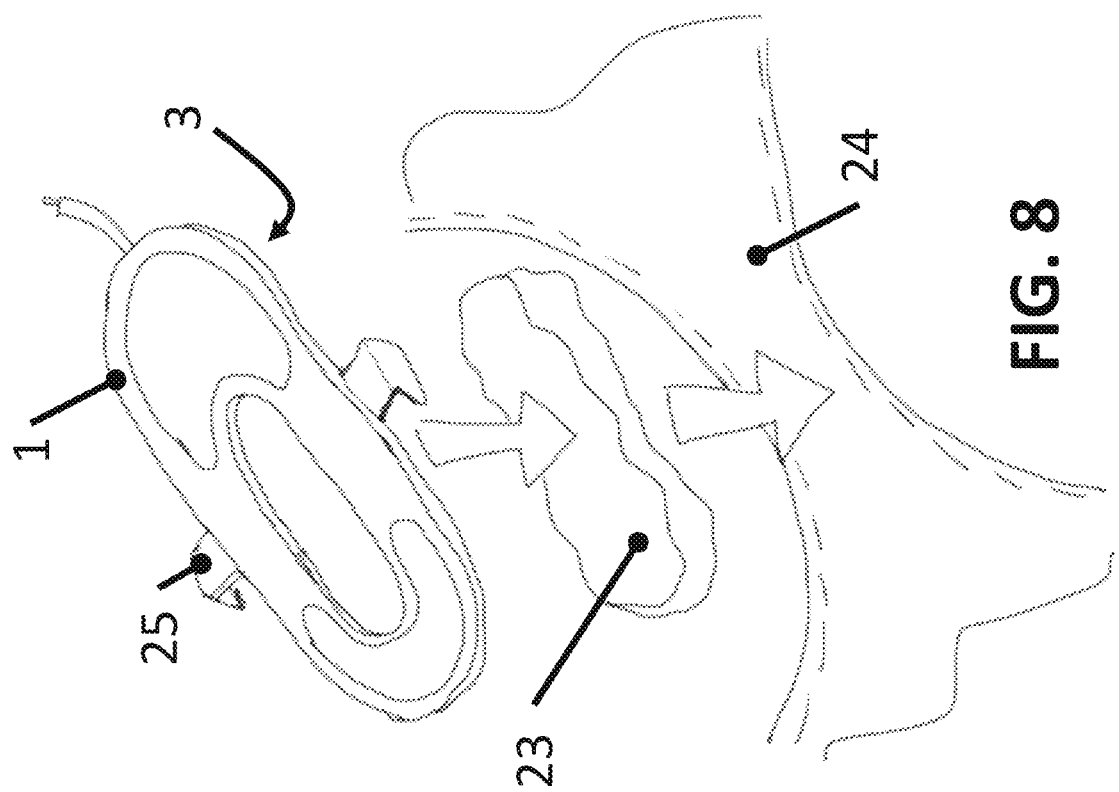
FIG. 8 is an exploded perspective view of an electrode embodiment.

Referring to FIG. 8, in one embodiment the outward facing surface 3 (i.e. non-skin contacting surface) of the electrode 1 includes an attachment portion enabling the user to temporarily affix the electrode to an underlying absorbent pad 23 or undergarment 24. Exemplary features include adhesives, plastically deformable tabs 25 and hook and loop fasteners.

Figure 9:
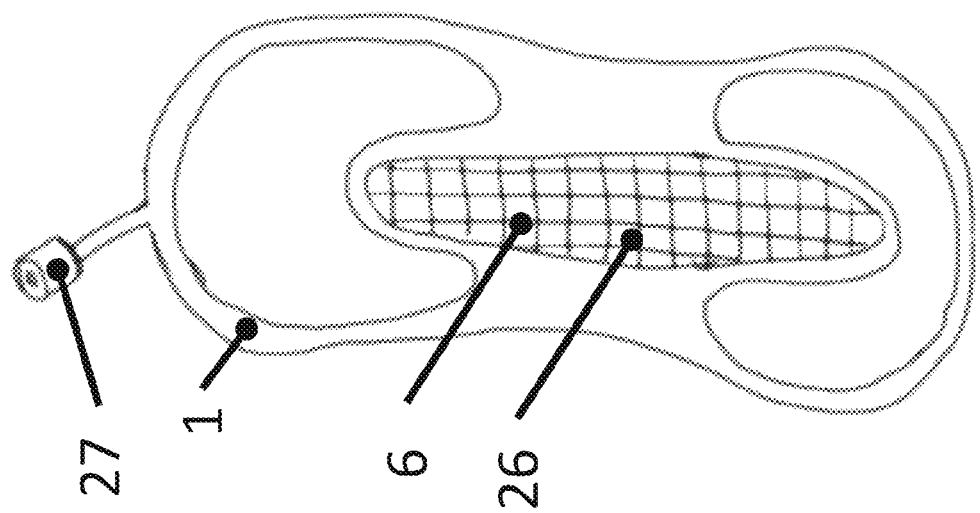
FIG. 9 is a view of an electrode embodiment.

Referring to FIG. 9, in certain embodiments the egress 6 through which bodily fluids pass is completely open. In other embodiments that space is occupied by a permeable structure through which the bodily fluids may pass, for example an open mesh 26. The mesh provides a degree a structure to the electrode 1 to maintain its shape and aide in placement. In another embodiment the back surface of the permeable structure comprises an adhesive to aide in temporarily affixing the electrode to an underlying absorbent pad 23 or undergarment 24.

Figure 10:
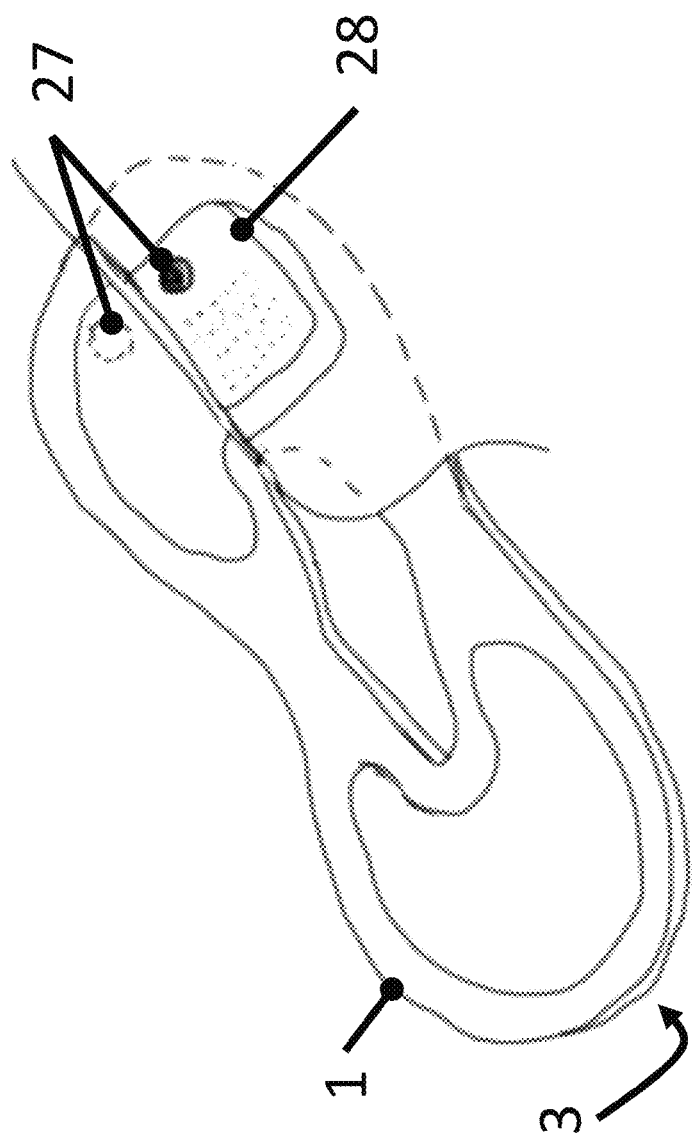
FIG. 10 is a cutaway perspective view of an electrode embodiment.

The electrode comprises one or more connectors 27 for connecting the electrode to a control unit (or pulse generator). Exemplary connectors include pins and snaps. Further, the electrode comprises conductive elements that permit current flow from the connector to the conductive region(s). With embodiments that include an anode and cathode within a single electrode, the conductive elements are insulated from one another within the electrode. These conductive elements may be wires or other conductive media including carbon or silver films. In certain embodiments the connectors 27 are provided at the end of wire leads with a length sufficient to reach the EMS device. In other embodiments the connectors 27 are located directly on the skin contacting surface 2 or outward facing surface 3 of the electrode 1. Referring to FIG. 10, in one embodiment the connectors 27 allow the EMS device 28 to be secured against the outward facing surface in the vicinity of the perineal tissues. In one embodiment the wire leads leading to anode and cathode form a single cable with one or more connector to the EMS device.

Figure 11:
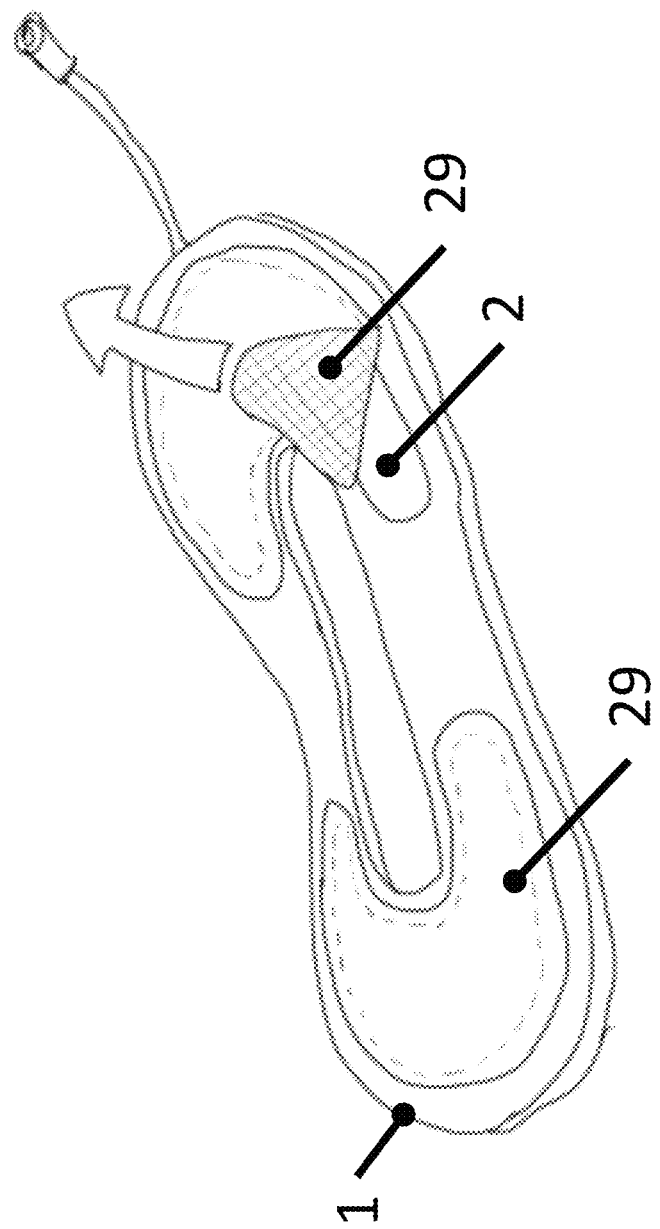
FIG. 11 is a perspective view of an electrode embodiment.

The electrode may be configured as either a disposable device or a reusable device. With the disposable configuration the user would wear the electrode for one day or several days and then discard it and use another electrode thereafter. With the reusable device configuration the user would clean the electrode between uses and use it for an extended period of time, for example, more than 1 week. Referring to FIG. 11, to facilitate cleaning of the reusable electrode 1, one embodiment includes an electrically conductive thin film cover 29 component that is placed on the skin contacting surface 2 and replaced between uses. This thin film cover 29 may include one or more adhesive sides to facilitate positioning relative to the electrode and contact with the skin. In one embodiment the thin film could be a hydrogel. To enhance reusability portions of the device may be comprised of silicone or similar durable and pliable polymer. The outward facing non-contact surface 3 may be substantially non-electrically conductive polymer. The skin contacting surface 2 may be comprised of both electrically conductive and non-conductive polymers. The electrode may be fabricated through multiple molding operations. These multiple molding operations may include over-molding portions of the electrode over wires.

Figure 12:
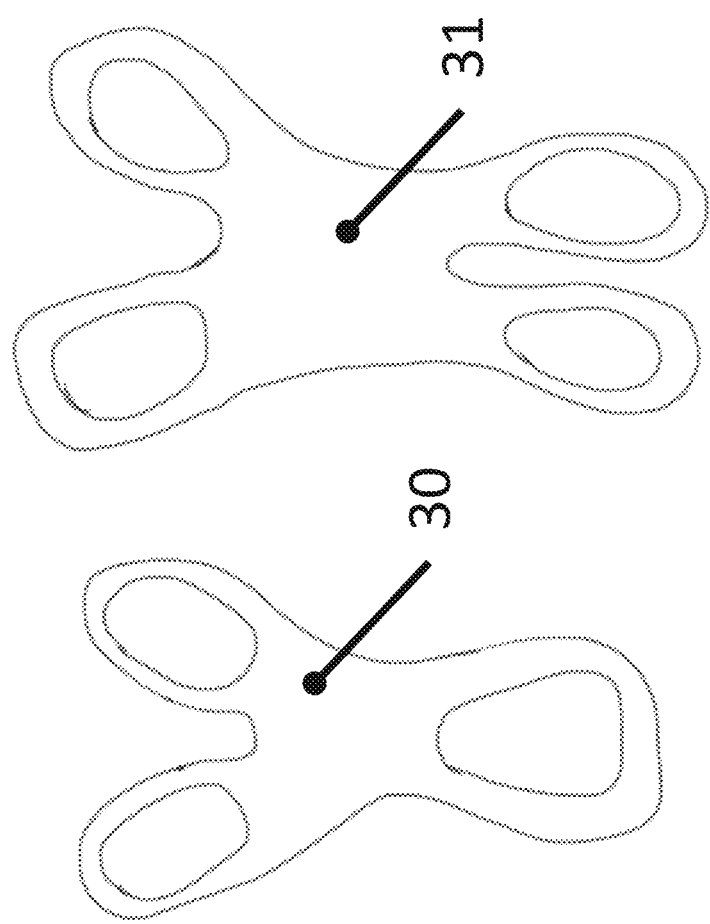
FIG. 12 shows two electrode embodiments of varying configurations.

Several of the aforementioned embodiments are best suited for use on female anatomy. Referring to FIG. 12, additional embodiments that accommodate male anatomy take the form of a "Y" 30 or "X" 31, and although an egress is not present, many of the aforementioned features that maintain prolonged contact between the electrode and skin are present. Further, the "Y" 30 shaped electrode can be configured such that the stem portion of the "Y" extends posteriorly toward the low back and positioning at least one conductive region 4 to stimulate the pudendal nerve.

Figure 13:
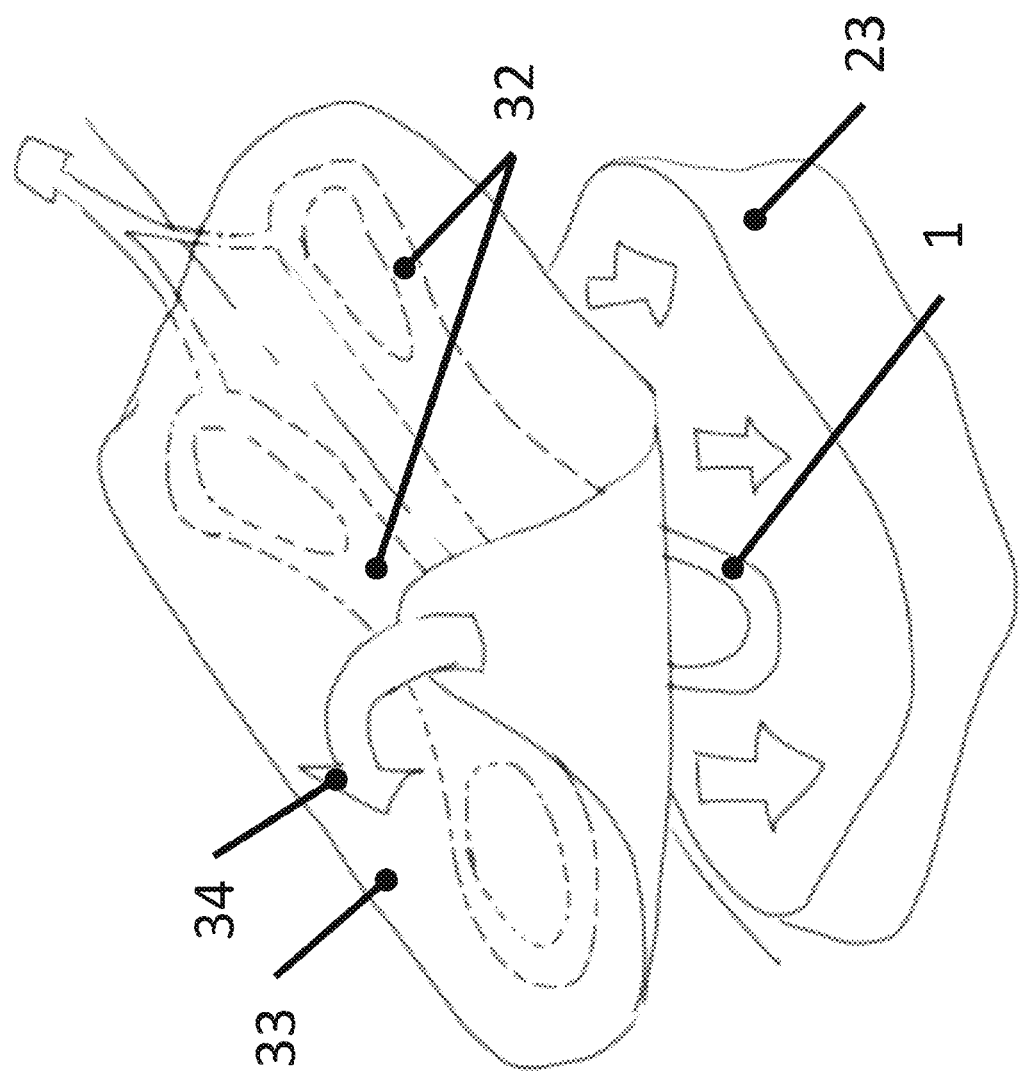
FIG. 13 is an exploded perspective view of an electrode embodiment.

Similarly, the device may comprise a pair of electrodes that mirror one another and are shaped to fit the perineal tissue with a space in between that would allow egress of bodily fluids. Referring to FIG. 13, in one embodiment this electrode pair 32 is removably connected to a transfer sheet 33. The transfer sheet 33 maintains the relative position of the individual electrodes 1 during electrode positioning and is subsequently removed 34. In another embodiment each electrode 1 in the electrode pair 32 adheres to an absorbent pad 23 or undergarment.

In another embodiment electrode 1 is removably connected to transfer sheet 33. Here, transfer sheet 33 facilitates handling and positioning of the device by the user. One method of applying the device includes steps of (1) partially peeling the transfer sheet 33 away from the electrode, (2) positioning the exposed portion of the electrode 1 against the skin, (3) fully peeling the transfer sheet 33 away from the electrode 1 and (4) securing the entirety of the electrode 1 against the skin. The transfer sheet 33 may have a shape and surface area substantially larger than the electrode 1 (shown) or have a shape and surface area substantially similar to the electrode 1. The transfer sheet 33 may comprise a handling tab that facilitates positioning and separation from the electrode 1. The transfer sheet 33 may include markings that facilitate positioning of the electrode 1 by providing anatomical references. The transfer sheet 33 may additionally provide a means for maintaining hydration and/or tack of the skin contacting surface 2.

Throughout this disclosure, use of the term perineal tissue is not meant to limit application of this invention to a precise area. For example, with certain embodiments a portion of the electrode may extend anterior, posterior or laterally to the perineum, with a goal of positioning the conductive regions at anatomic sites best suited for transmitting current to the pelvic floor.

Figure 14:
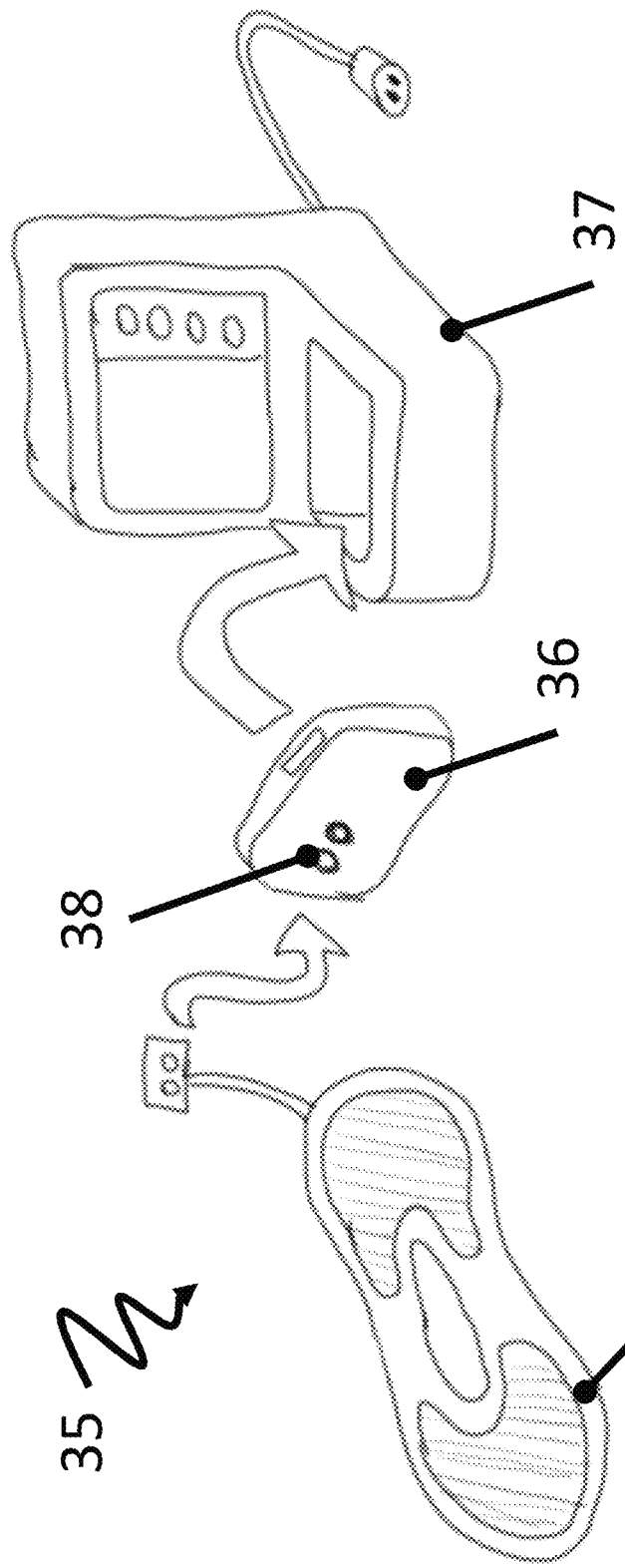
FIG. 14 is a perspective view of an incontinence treatment system.

Referring to FIG. 14, another embodiment of the invention is an incontinence treatment system 35 comprising the aforementioned electrode 1 and a wearable pulse generator 36. The wearable pulse generator 36 produces a prescribed electric waveform and delivers it to the electrode 1. The wearable pulse generator 36 comprises a battery, a microprocessor, a step-up transformer, and an outer housing. Additionally, the wearable pulse generator 36 includes one or more connectors 38 suitable for connecting to the electrode 1. The outer housing and connectors of the wearable pulse generator 36 are substantially water resistant, permitting use in direct contact with skin during which the device may be exposed to bodily fluids. In another embodiment the incontinence treatment system 35 additionally comprises a docking station 37 that serves to recharge and/or program the wearable pulse generator 36.

The wearable pulse generator, like the electrode, is configured for extended wear, allowing the user to wear the component on his person for multiple hours and between treatment sessions-due to its size, weight and contour. In certain embodiments, the wearable pulse generator is concealable within or under the user's clothing. Similarly, maintaining a relatively small physical volume contributes to successful concealment. In one embodiment these features are achieved by using a flat battery configuration. In another embodiment this is achieved by using a planar step-up transformer. In another embodiment this is achieved by minimizing the number and size of user control features (e.g. buttons, dials, lights, graphic displays, touchpads) on the wearable pulse generator. In another embodiment the wearable pulse generator includes a user control feature that when activated acts to suspend or delay EMS treatment. In another embodiment the user controls device settings through a smart phone device via an app or web-based interface.

The housing of the wearable pulse generator includes a feature for situating the component within or under the user's clothing. In one embodiment this is a clip, latch or closure configured to interface with the user's garment along the waistline. In another embodiment the position of the wearable pulse generator is maintained with an adhesive.

In another embodiment a skin contacting surface of the housing provides a conductive region suitable for establishing current between it and a conductive region on the electrode. For example, current flows from an anode on the electrode, through tissue and to a cathode on the housing.

In one embodiment, when not being worn the wearable pulse generator is connected to a docking station that acts to recharge the battery of the wearable pulse generator. In one embodiment the docking station provides an interface through which the user can visualize and manipulate device setting including treatment waveform, intensity, and treatment schedule (e.g. when to begin treatment, for how long, how many times per day). The interface may include buttons, dials, lights, graphic displays and touchpads.

Throughout this disclosure use of the term electric muscle stimulation (EMS) is not intended to limit the scope of the invention. Similarly, differing specific terms or means of contracting targeted muscles that are considered interchangeable include functional electrical stimulation (FES), transcutaneous electrical nerve stimulation (TENS) and interferential currents (IF). Further, the terms anode and cathode are used to designate directionality of current flow. Their use is not meant to limit the scope of applicable embodiments to a specific anode-cathode orientation. Rather, it is understood that in many instances the directionality of current flow could be reversed while achieving the same clinical benefit. Further, bipolar waveforms can be used such that each conductive region serves as both anode and cathode over the course of treatment.

Figure 15:
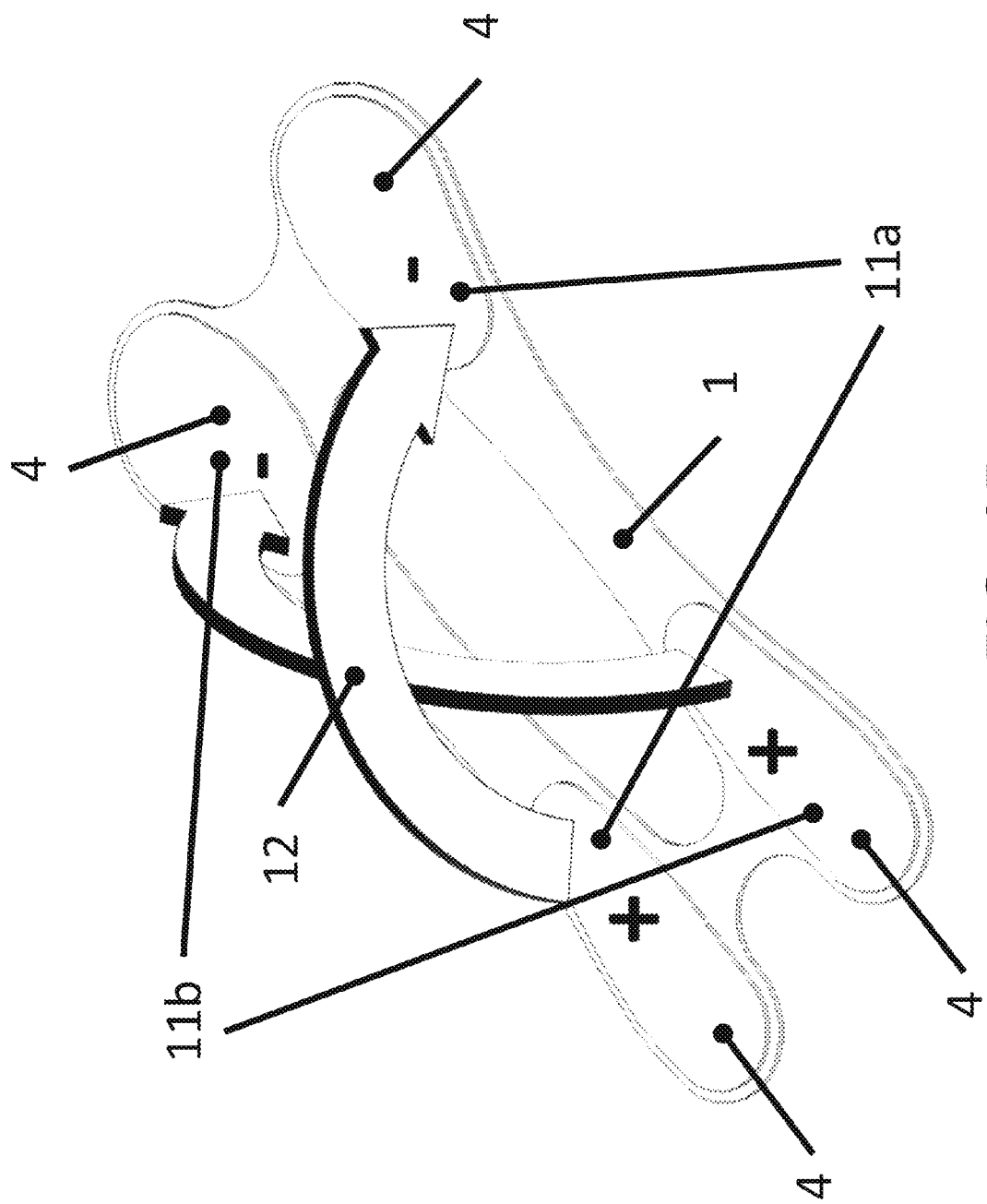
FIG. 15 is a schematic view of an electrode embodiment.

More specifically, interferential currents have been found to provide a particularly effective treatment. IF currents utilize two intersecting anode-cathode pairs operating at different output frequencies such that their resulting interference signal generates a local beat frequency at a targeted location within the tissue. The output frequencies are selected to maximize tissue penetration depth and minimize skin surface, while the beat frequency is paced to stimulate the targeted muscles. By way of non-limiting example, a first anode-cathode pair may operate at 4000 Hz and a second anode-cathode pair may operate at 4050 Hz, resulting in a beat frequency of 50 Hz. Preferred embodiments of the disclosed electrode device operating with IF current have a difference between the first and second frequencies (i.e., beat frequency) within the approximate range of 1-150 Hz. Even more preferably, IF current operating embodiments have a beat frequency within the approximate range of 20-75 Hz, with one preferred embodiment operating with a beat frequency of about 50 Hz. Referring to FIG. 15, in one embodiment electrode 1 is comprised of four conductive regions 4 forming two anode-cathode pairs 11a and 11b oriented such that their respective currents intersect 12.

Figure 16:
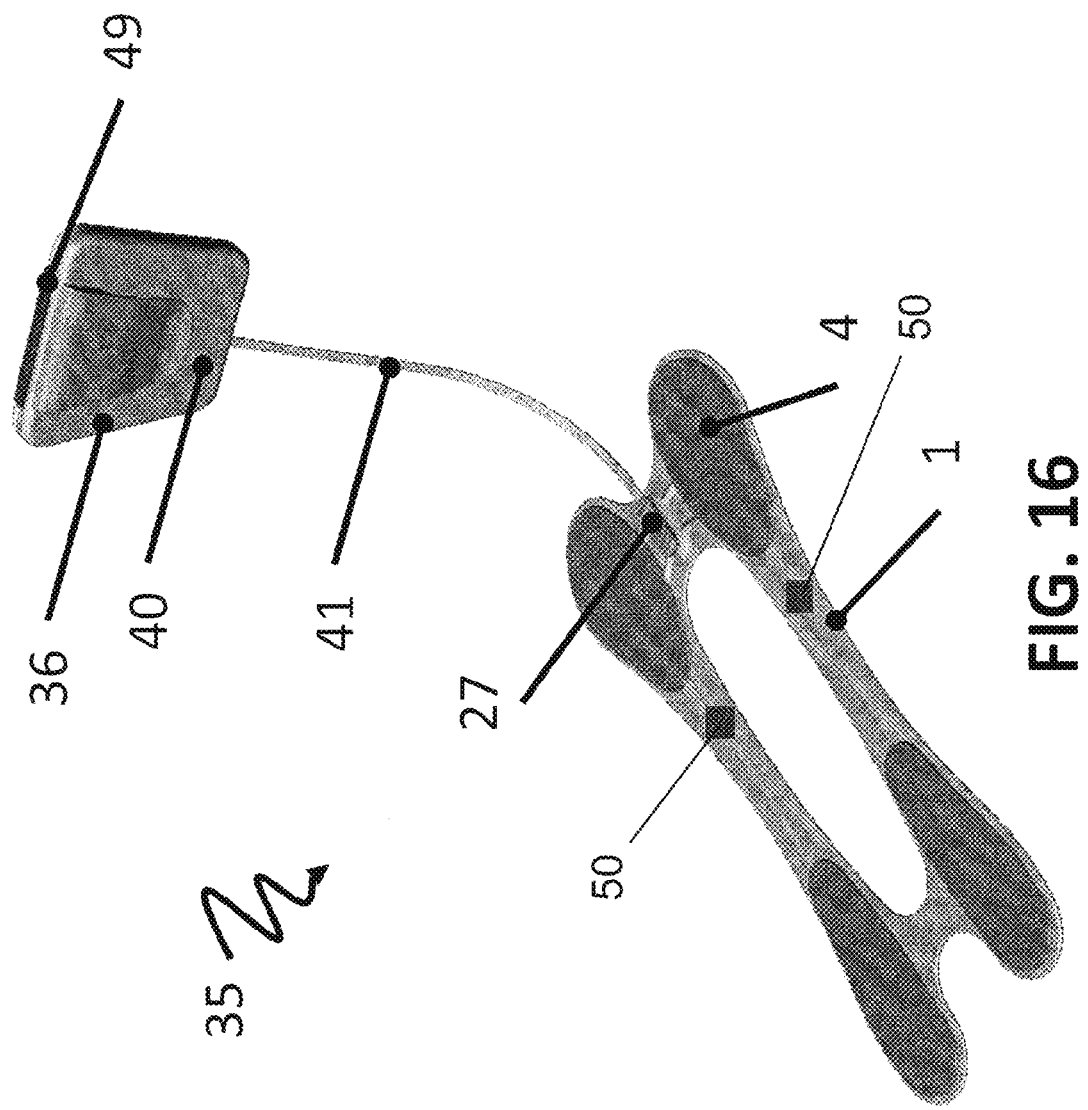
FIG. 16 is a rendering of an incontinence treatment system.

FIG. 16 shows another embodiment of the incontinence treatment system 35 comprising an electrode 1 and wearable pulse generator 36. Here the electrode 1 is comprised of four conductive regions 4. Connection between the electrode 1 and the housing 40 of wearable pulse generator 36 is achieved through cable 41. Cable 41 includes one or more connectors 27. In one embodiment at least one connector 27 forms a detachable connection with the electrode 1 or wearable pulse generator 36. In another embodiment cable 41 is detachably connected to both the electrode 1 and wearable pulse generator 36. In another embodiment the incontinence treatment system 35 is comprised of more than one cable 41 provided in different lengths suitable to accommodate a range of patient anatomies and placement locations of the wearable pulse generator 36.

Figure 17:
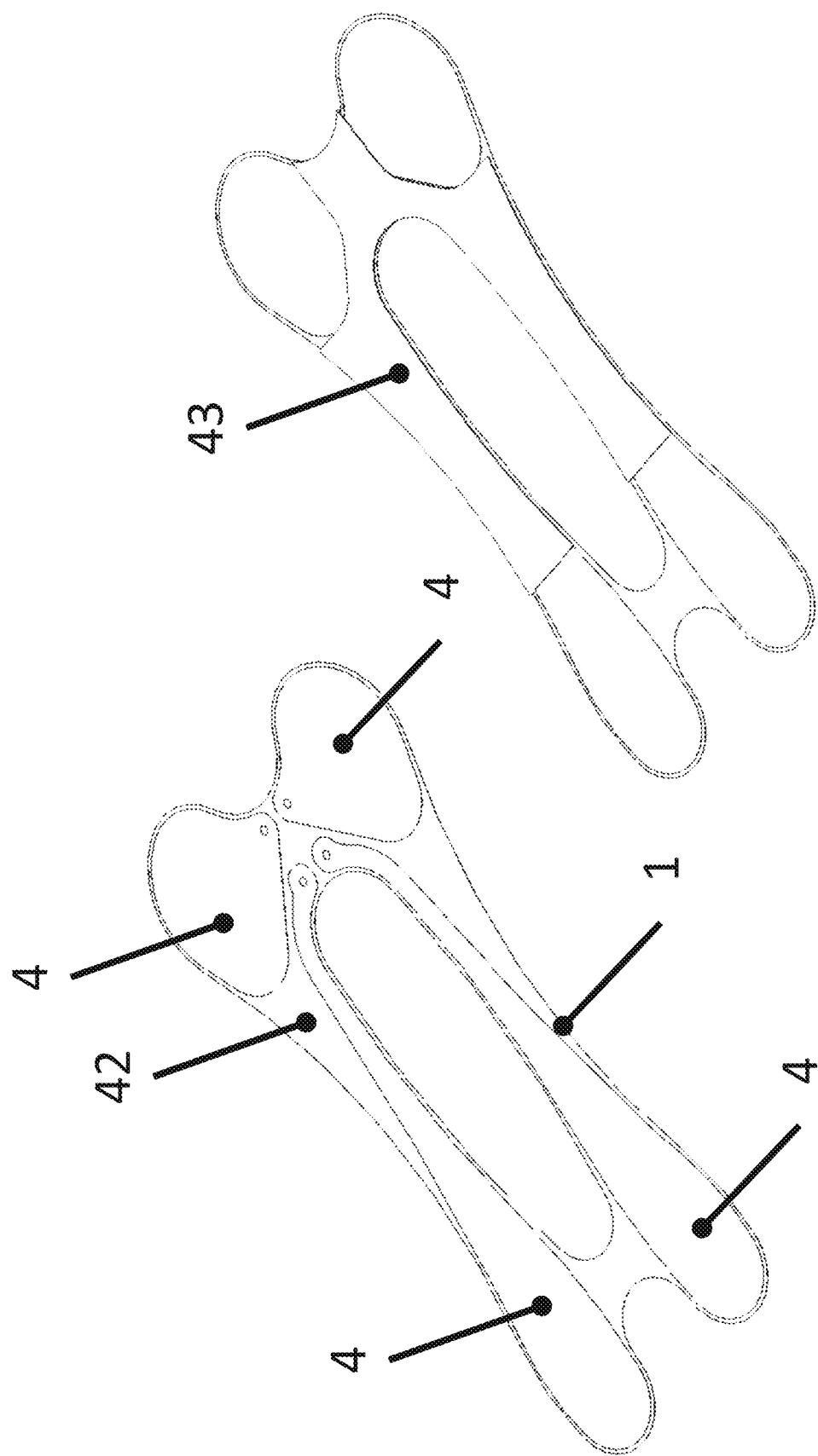
FIG. 17 provides perspective views of a multi-layered electrode embodiment.
Figure 18:
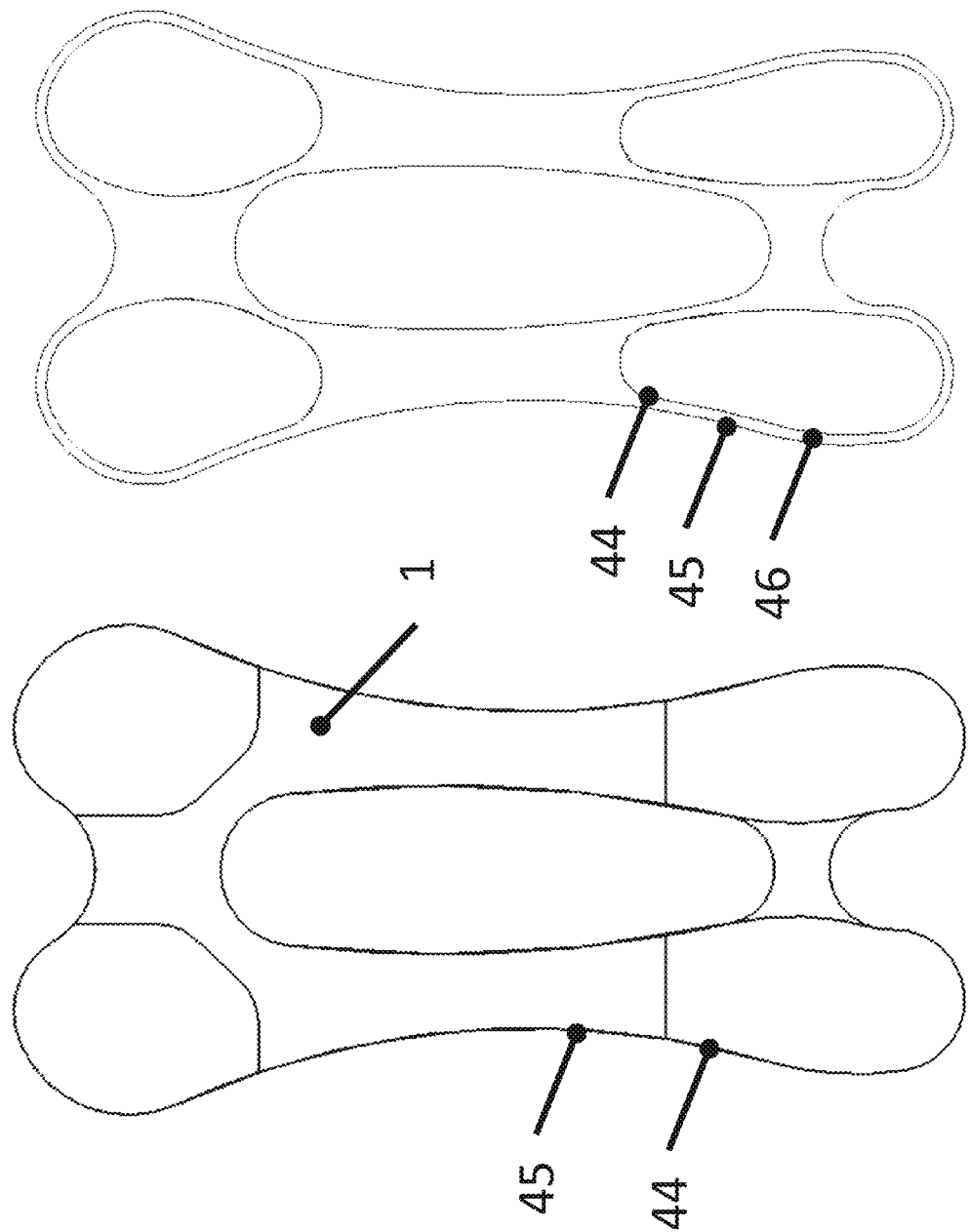
FIG. 18a and FIG. 18b are views of electrode embodiments.

FIG. 17 depicts an embodiment of electrode 1 in which four conductive regions 4 are provided on a non-conductive substrate 42. The conductive regions 4 are provided in an arrangement such that portions of each conductive region 4 are co-located and provide continuity to connector 27. In one embodiment connector 27 comprises a plurality of snap-fit button features. Further, a portion of one or more conductive regions is covered by an electrically insulating layer 43. This composition is potentially beneficial in that it eliminates the need for wires within electrode 1, thereby reducing manufacturing cost. FIG. 18a depicts an embodiment of electrode 1 with four conductive regions 4. By way of non-limiting example, the electrode has dimensions of 20 cm long by 10 cm wide, providing an electrode aspect ratio (i.e. length/width) of 2:1. Further, egress 6 has a length of 10 cm and a width of 3.3 cm, providing an egress aspect ratio of 3:1. Further, conductive regions 4 are spaced 2 cm apart in a lateral direction and 8 cm apart in the longitudinal direction. Other embodiments may have electrode aspect ratios of greater than 1.5:1, egress aspect ratios of greater than 2:1, lateral spacing of conductive regions greater than 1 cm and longitudinal spacing of conductive regions greater than 5 cm. In another embodiment one or more anterior conductive region 47 are wider than one or more posterior conductive region 48. In another embodiment one or more posterior conductive region 48 is longer than one or more anterior conductive regions.

FIG. 18a depicts an embodiment with conductive region edges 44 that are contiguous with electrode edges 45. FIG. 18b depicts an embodiment of electrode 1 wherein the conductive region edges 44 are offset from the electrode edges 45. The margin 46 defined by the space between the conductive region edges 44 and the electrode edges 45 may comprise a portion of the non-conductive region 5. In certain embodiments margin 46 is configured to isolate the conductive regions 4 from bodily fluids. In another embodiment gasket 22 is formed around the periphery of one or more conductive regions 4.

In another embodiment electrode 1 is formed as a multi-layered construct wherein an electrically conducting element in continuity with a first conductive region passes under and is electrically isolated from a second conductive region. In another embodiment the electrically conducting element is a wire. In another embodiment the electrically conducting element is a layer of conductive medium.

In one embodiment of the electrode a multilayered construct includes a stiffening member proximate the conductive region 4, providing a construct with relatively more rigidity near the conductive regions 4 and relatively less rigidity near the non-conductive regions 5. In one embodiment the non-conductive region provides for a measure of elasticity.

Figure 19:
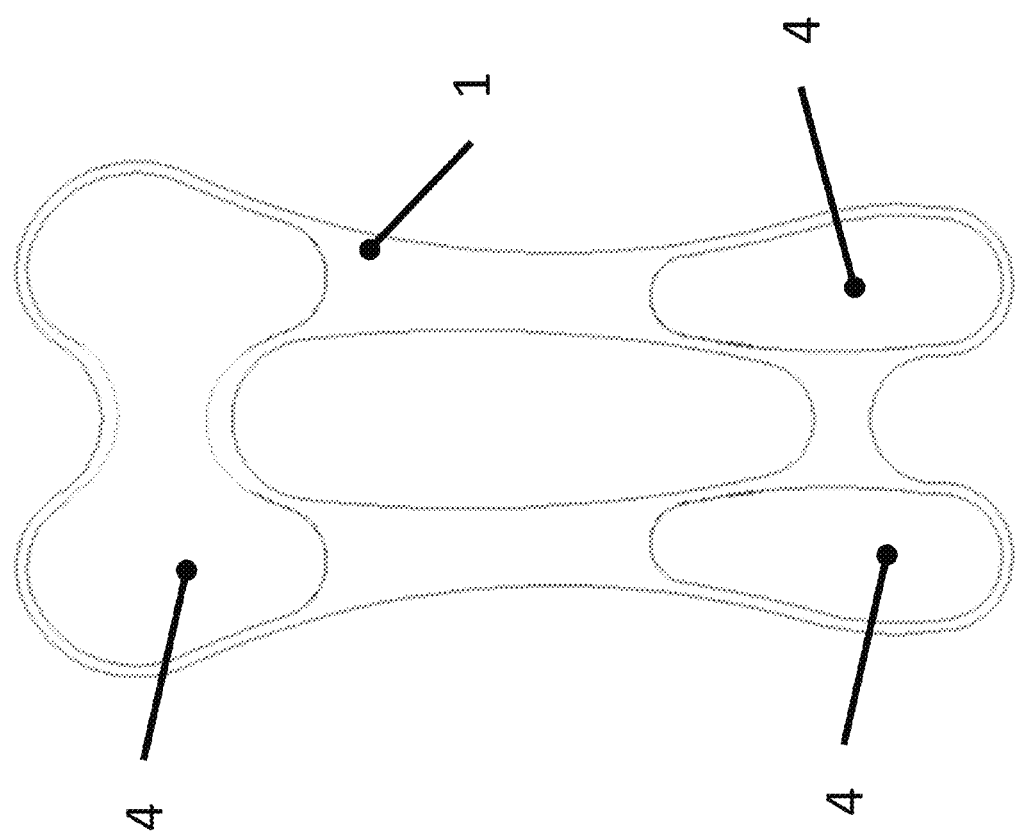
FIG. 19 is a view of an electrode embodiment.

Referring to FIG. 19, in an embodiment suitable for EMS, the electrode 1 is comprised of three conductive regions 4.

Referring back to the incontinence treatment system 35 of FIG. 16, wearable pulse generator 36 includes button 49 that serves as a means for the user to interface with the wearable pulse generator 36. The button 49 may be located on the top edge of the housing (shown) or other patient accessible surface. The button 49 may serve one or more functions selected from a group including power on, power off, defer treatment, extend treatment, increase intensity and decrease intensity. In another embodiment more than one button 49 is provided on the wearable pulse generator 36. Certain embodiments of the wearable pulse generator 36 include a rechargeable battery and means of connecting the wearable pulse generator to a recharging element.

Another embodiment of the invention includes a method for treating incontinence comprising treatment blocks during which the electrode 1 described herein is worn continuously and wherein each treatment block is comprised of sequential periods of active and inactive treatment. By way of non-limiting example, a treatment block may comprise 8 hours during which a user continuously wears the electrode 1. During this treatment block treatment (i.e. pelvic muscle floor training or toning provided by inter alia EMS, TENS, or IF) is provided in 10 minute intervals separated by 50 minutes of inactivity, during which the electrode 1 is not delivering treatment. Other embodiments include block treatment times of 1-12 hours, active treatments durations of 5-30 minutes and inactive durations of 10-120 minutes. This automated treatment method is beneficial in that is facilitates multiple treatment sessions without requiring the user to purposefully initiate each active treatment session.

In certain embodiments the duration of treatment blocks and active/inactive periods is controlled through a user interface. This user interface may comprise software accessible as a computer program or mobile device application. This software can provide the ability to track device usage across multiple treatment blocks and report data to the user or healthcare professional.

Certain embodiments of the incontinence treatment system 35 include one or more sensors proximate the outward facing surface 3 of the electrode 1 and configured to measure the moisture content of an adjacent absorbent pad. This moisture content data can be subsequently used to monitor leakage during the course of treatment, both in the short term (i.e. within a treatment block) and the longer term (i.e. between treatment blocks). In this way the user or healthcare professional can track efficacy of the treatment. Monitoring a change in electrical impendence is an exemplary means of detecting moisture. Measuring temperature change is another exemplary means of detecting moisture.

Similarly, certain embodiments may include one or more sensors 50 proximate the skin contacting surface that monitor the presence of moisture near the conductive regions. The presence of excessive moisture in this region may adversely affect the intended electrical continuity at the skin-electrode interface. By appreciating the level of moisture content an internal algorithm can determine whether to initiate and/or stop treatment or to adjust signal intensity levels, all in an effort to provide optimal treatment and safety.

Certain embodiments may monitor bioelectric feedback to identify when and to what degree the pelvic floor muscles are contracting. This bioelectric feedback may be received through the conductive regions 4 or through separate sensor elements. This information is useful in assessing the short-term and long-term efficacy of the treatment. In one embodiment, when muscle contraction response to a given applied current falls below a set limit the treatment is concluded. In another embodiment, when muscle contraction response to a given applied current falls below a set limit the signal intensity is increased. In another embodiment, intensity level is automatically adjusted to minimally exceed the activation level of the target musculature.

In another embodiment the device is configured to be worn while the user sleeps. The corresponding treatment block delivers one or more active periods, wherein the first active period begins after the user has fallen asleep and at an intensity level that does not wake the user. In one embodiment the initiation of this first active period is controlled by a timer. In another embodiment initiation of the first active period is controlled by a sleep monitor feature that identifies when the user has fallen asleep. Such sleep monitor features are known elements of wearable wellness devices. In another embodiment the sleep monitor feature continuously monitors the user's sleep pattern and delivers multiple active treatments when the user is in the deepest sleep cycles. In another embodiment, prior to going to sleep the user executes a program that confirms suitable placement and intensity level settings of the device such that when the device enters the first active period it will deliver treatment per intent. In another embodiment, the treatment starts before the user has fallen asleep.

In a similar manner, the incontinence treatment system 35 can monitor impedance through the conductive regions before, during and after active treatment. Changes in impedance can be used to determine whether one or more conductive regions has diminished skin contact. When this occurs, the system can stop or prevent treatment and signal the user to modify placement of the electrode.

In another embodiment, appreciating that less activation energy is required to contract toned muscles, the system monitors the intensity of muscle contraction as a function of signal intensity. This data can then be used to quantify the response to treatment both within a treatment block and between treatment blocks. Further, this data may be used to auto adjust the signal intensity level provided by the signal generator.

While a preferred embodiment has been set forth for purposes of illustration, the foregoing description should not be deemed a limitation of the invention herein. Accordingly, various modifications, adaptations and alternatives may occur to one skilled in the art without departing from the spirit of the invention and scope of the claimed coverage.

What is claimed is:

1. An electrode device for use in treating incontinence in an individual or animal, comprising:
   a body having a contact side and a non-contact side, extending longitudinally between a first end and second end, and defining a medial egress from the contact side to the non-contact side;
   two or more activatable conductors spaced from each other and positioned around the periphery of the egress on the contact side of the body and being electrically insulated from the non-contact side; wherein
   the contact side defines a surface and profile configured for interfacing with perineal tissue in a position with the medial egress aligned and external to a ureteral or vaginal opening of the individual or animal, whereby electrical current generated through the conductors is allowed to penetrate the perineal tissue and stimulate at least one muscle therein in the individual or animal, and the medial egress allows bodily waste to be excreted from the ureteral or vaginal opening through the egress without obstruction.

2. The electrode device of claim 1, comprising at least three conductors.

3. The electrode device of claim 1, wherein the conductors comprise at least two cooperative anode-cathode pairs.

4. The electrode device of claim 1, wherein the body defines an outer peripheral edge that transitions inwardly toward an intermediate portion between the first and second ends.

5. The electrode device of claim 1, wherein the contact side of the body includes a non-conductive region for fluidly isolating the conductors from fluid passing through the egress.

6. The electrode device of claim 1, wherein the egress extends longitudinally through one end of the body.

7. The electrode device of claim 1, comprising a moisture sensor positioned within a non-conductive region of the body.

8. The electrode device of claim 1, wherein the egress has a longitudinal length to width aspect ratio within the range of 2:1 to 4:1.

9. The electrode device of claim 1, comprising two pair of activatable conductors.

10. The electrode device of claim 9, wherein each pair of activatable conductors comprises a cathode region and an anode region.

11. The electrode device of claim 1, wherein the body extends longitudinally through one of the first end or second end.

12. The electrode device of claim 1, wherein the egress is positioned between opposite lateral edges of the body.

13. The electrode device of claim 1, wherein the medial egress extends along a sagittal plane and at least one conductor is positioned on each side of the sagittal plane.

14. The electrode device of claim 1, wherein the medial egress defines an edge that resists flow of bodily fluid.

15. The electrode device of claim 1, wherein the outer periphery of the egress comprises a gasket to assist in resisting flow of bodily fluid passing through the egress.

16. The electrode device of claim 1, wherein a first of the at least two conductors is spaced from a second of the at least two conductors with the egress intermediate the first and second of the at least two conductors.

17. An electrode device for use in treating incontinence in an individual or animal, comprising:
 a body extending longitudinally between a posterior end and an anterior end, the body defining an outer peripheral edge having a generally hourglass shape wherein the lateral width narrows between the posterior end and anterior end, the body having a contact side and a non-contact side and defining a medial egress from the contact side to the non-contact side;
 at least one activatable anterior conductor positioned on the contact side of the body proximate the anterior end substantially electrically insulated from the non-contact side;
 at least one activatable posterior conductor positioned on the contact side of the body proximate the posterior end being substantially electrically insulated from the non-contact side and at least one anterior conductor, wherein at least one anterior conductor and at least one posterior conductor are spaced from each other and positioned around the periphery of the egress, the contact side defines a surface and the hourglass peripheral shape allows for interfacing of the contact side surface with perineal tissue in a position with the medial egress aligned and external to a ureteral or vaginal opening in the individual or animal with the at least one posterior conductor in electrical communication with the at least one anterior conductor, whereby an electrical current generated between the conductors penetrates the perineal tissue to stimulate at least one muscle therein and bodily waste is allowed to be excreted freely from the ureteral or vaginal opening through the egress.

18. The electrode device of claim 17, comprising at least one insulated region in the contact side of the body positioned intermediate the medial egress and each of the anterior and posterior conductors.

19. The electrode device of claim 17, wherein the at least one posterior conductor and at least one anterior conductor each has a portion that is co-located with one another to provide electrical continuity to a common electrical connector.

* * * * *

UNITED STATES PATENT AND TRADEMARK OFFICE
CERTIFICATE OF CORRECTION

PATENT NO. : 9,623,231 B2  Page 1 of 1
APPLICATION NO. : 14/678058
DATED : April 18, 2017
INVENTOR(S) : Eric Kolb and Gloria Kolb It is certified that error appears in the above-identified patent and that said Letters Patent is hereby corrected as shown below:

On the Title Page

(73) Assignee:
Delete "Elidah, LLC, Sandy Hook, CT (US)" and insert --Elidah, Inc., Monroe, CT (US)--

Signed and Sealed this
Thirteenth Day of June, 2017

Joseph Matal
*Performing the Functions and Duties of the*
*Under Secretary of Commerce for Intellectual Property and*
*Director of the United States Patent and Trademark Office*